US006993140B1

(12) United States Patent
Chen

(10) Patent No.: US 6,993,140 B1
(45) Date of Patent: Jan. 31, 2006

(54) 3-IN-1 ANTI-NOISE RADIO SOUND-COLLECTION DEVICE

(76) Inventor: Jinsaun Chen, 2nd Floor, No. 8 & 10, Lane 337, Yung Ho Road, Chung Ho City, Taipei (TW)

( * ) Notice: Subject to any disclaimer, the term of this patent is extended or adjusted under 35 U.S.C. 154(b) by 0 days.

(21) Appl. No.: 09/069,947

(22) Filed: Apr. 30, 1998

(51) Int. Cl.
*A61F 11/06* (2006.01)
*H04R 1/10* (2006.01)
*H04R 5/02* (2006.01)

(52) U.S. Cl. ........................ 381/71.6; 381/74; 381/311

(58) Field of Classification Search ............... 381/71.1, 381/74, 71.6, 94.1, 310, 2–3, 311; 379/430; 700/94
See application file for complete search history.

(56) References Cited

U.S. PATENT DOCUMENTS 4,412,106 A * 10/1983 Pavel ......................... 381/309
5,604,813 A * 2/1997 Evans et al. .................. 381/71
5,647,011 A * 7/1997 Garvis .......................... 381/74
5,666,658 A * 9/1997 Borchardt et al. ............ 455/42
5,887,066 A * 3/1999 Nakagawa .................. 381/311
6,035,047 A * 3/2000 Lewis ......................... 381/74
6,061,456 A * 5/2000 Andrea et al. ............. 381/71.6
2001/0050993 A1 * 12/2001 Douglas .................... 381/71.6

* cited by examiner

*Primary Examiner*—Laura A. Grier
(74) *Attorney, Agent, or Firm*—Donald C. Casey

(57) ABSTRACT

A headphone mounted 3-in-1 anti-noise radio sound-collection device is described. The device includes an anti-noise circuit system, a radio am/fm circuit system, and a sound collection system for receiving an external sound. The structure is wireless with a microphone and associated cables contained in the headphone headband. The microphone is provided to receive an external noise signal, and the device then generates a nullifying out of phase signal. The device uses a sound collection device to receive an external signal and an am/fm radio is also provided, all of which sound through the ear speakers on the headphone.

1 Claim, 7 Drawing Sheets

3-IN-1 ANTI-NOISE RADIO SOUND-COLLECTION DEVICE

The "3-in-1 Anti-Noise Radio Sound-Collection Device", a kind of headphone device, is a new invention which integrates functions of anti-noise circuit system, radio circuit system and sound-collection circuit system into a 3-in-1 circuit system. This device not only eliminates the noise hurt to human ears while in a high noise polluted environment but also receives the radio broadcast program or other external audio input clearly. There are more versatility, adaptability, and practicabi in using of this device. In anti-noise circuit system, the microphone that receives the external noise is connected directly to the headphone structure to form a unify structure. The headband leading cable i hide in the Headband so that the outlooking of this device is a wireless structure. Not like the ordinar headphone, which has a separated microphone connecting to it, the wireless structure of this invention can eliminate the disadvantage of hindering some objects caused by the cable.

BACKGROUND OF THE INVENTION

1. Field of the Invention

The present invention relates to a headphone device which combine the functions of anti-noise, receiving radio broadcast program and sound collecting into one unit. It can protect human ears from the harm of noise in an environment of high noise pollution, and listen to radio program or other external audio input clearly.

2. Description of Related Art

With recent rapid progress of industry, current social structure is no more the same as it's in agricultural period. Labors are major populations so it's unavoidable that the labor rights rise accordingly. Labors in high noise pollution environment, such as airport, factories, etc, are exposed to different noises, I.e. engine sound of airplane, engine and cracks of heavy machines, the start of car or motor sounds. Working long time in such environments will hurt ear structure with no doubt. Therefore, protecting workers hearing is one of major issues in industrial safety: The general practice is to ask workers to wear ear seal or headphone at any time in the high noise environment. By doing so, we can lessen the noise intensity to a certain degree, but practically there are some inconveniences according to experience. First, in working environment, noise intensity varies from time to time. Either ear seals or headphones can only provide noise proof effectiveness with a fixed range. Their protection effectiveness will be greatly discounted and will be dissatisfying when there are some sudden high-intensity noises, which will cause chronic harm to ears, furthermore, communications in this environment will be another issue. Due to the noise interruption and the protection of ear seal or headphone, people can not communicate in an effective way. They can communicate each other only in a very close distance or by removing ear seals or headphone. So, it's very inconvenient, let alone listening to radio or external sound by headphone. To sum up, the used way to prevent noise for protection did not consider the convenience I usage and appliance and the protection effect is also poor, which did dissatisfy end users.

SUMMARY OF THE INVENTION

To manage the unexpected noise intensity changes, a microphone was used in the devise to receive outside noise and to detect its intensity and direction. A sound wave contrary to noise is exported from the speaker of earphones, which will have the effectiveness to offset when it is overlapped with noise wave. Thus, noise can be eliminated. This kind of earphone has better noise-proof effect than above mentioned pure ear seal but the microphone to receive noise is a separate portion and is usually equipped in the waste with a cable connecting to earphone.

However, due to the connection cable, users are tripped unintentionally physically so that the connection will loose and the earphone will have no effect sometimes, There is also discrepancies in usage. Therefore, the only noise-proof function can not meet various requirements from users, in term of this, the inventor is eager to find out a noise proof earphone equipment and also integrate the function of radio listening and the input of external sound sources. After numerous designs and tests, the present invention 3-in-1 Anti-Noise Radio Sound-collection come out. The present invention makes the microphone which receives outside noise and the earphone be one and adds the functions of radio and sound-collection to achieve the Three in One structure. It has simple appearance without the inconvenient connecting cable. In addition to good noise-proof effect, if can clearly tune in radio program and external sound sources. It's a multi-function design.

The description of the number used in the diagrams:

| | | | | | |
|---|---|---|---|---|---|
| (1) | Sleeve | (2) | Headband | (3) | Headband Leading Cable |
| (4) | Headset Elastic | (5) | Battery Cover | (6) | Battery Spring |
| (7) | Ear Cover | (8) | PCB Assembly | (9) | AB Clip |
| (10) | Speaker Cable | (11) | Speaker | (12) | Speaker Plate |
| (13) | Screw | (14) | Earcup Sponge | (15) | Channel Tuner |
| (101) | Microphone | (102) | Phase detection u-circuit IC | | |
| (201) | u-circuit IC | (202) | Down-Convert Circuit | (203) | Wave-detect Circuit |
| (204) | Demodulate Circuit | | (SW1)(SW2) Switches | | |
| (VR1), (VR2) Variable Resistor | | | | | |
| (301), (AUX) External Audio Input | | | | | |
| (R) Right Channel | | (l) Left Channel | | | |

DETAILED DESCRIPTION OF THE PREFERRED EMBODIMENT

Figure 1:
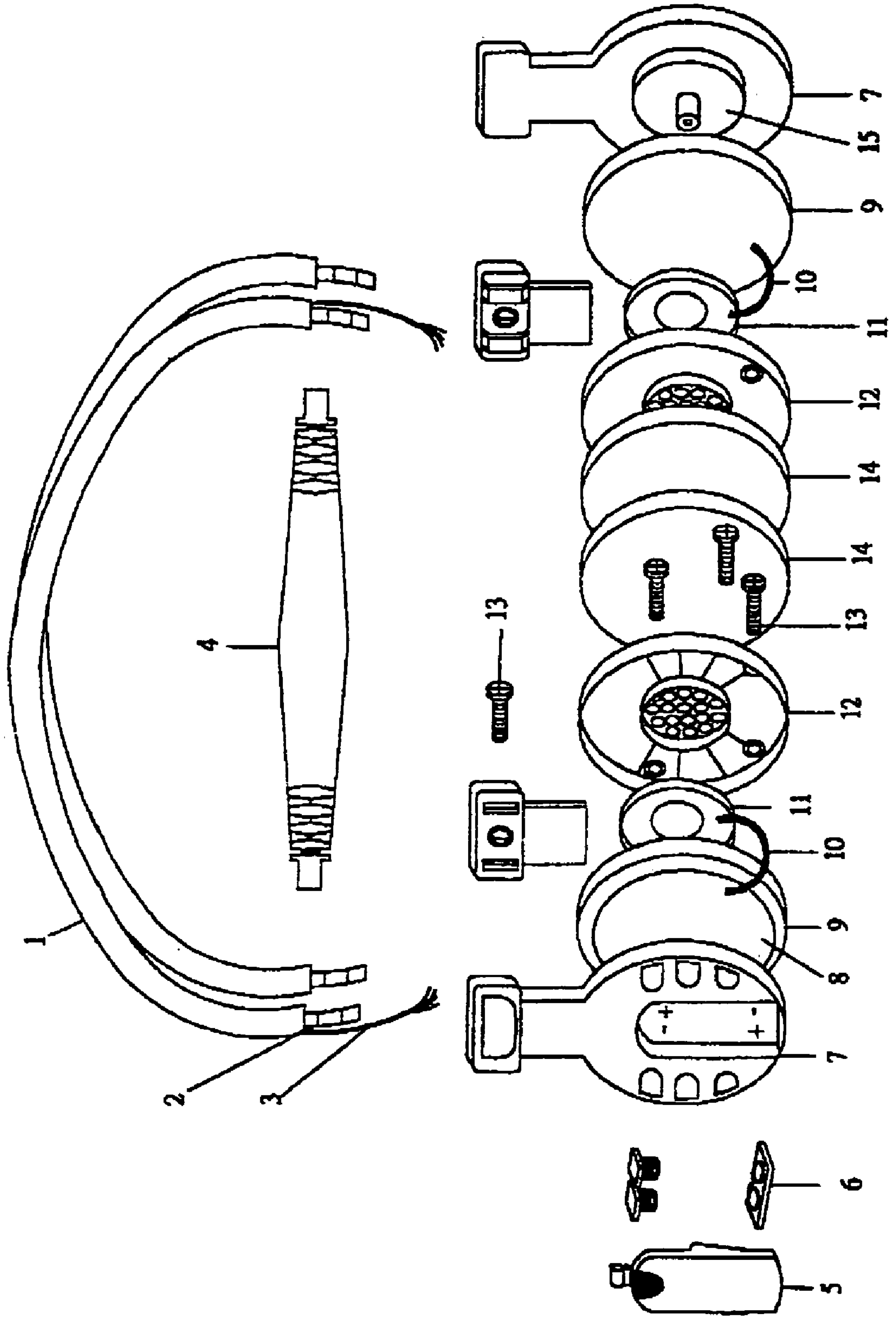
FIG. 1 is an exploded view of the device of this invention.

The FIG. 1 is the 3-d decomposition diagram of the present invention. Its structures are composed of a Headband(1) to connect the two headsets unit, a flexible Headband(2) to support the Headband(1) and a Headband Leading Cable(3) to connect the circuit boards of the two headset are inside the Headband(1), a Headset Elastic(4) to provide comfort usage. For one side of the headset, it compose of an Earcover(7). A speaker plate(12) a several screw(13). Between them, there is a PCB Assembly of action circuit, an AB Clip(9) and a Speaker(11). A Speaker Cable(10) is used to connect the Speaker(11) and the PCB Assembly(8). Also, there is a set of Battery spring(6) inside the battery room in the Earcover(7), and the battery room is covered by a battery Cover(5). The batteries are put in here to support the power of this device. Outside the Speaker Plate(12), an Earcup Sponge is used to provide the comfortable feeling while contacting with human ears. The structure of the other headset is almost the same except that a tuning channel tuner (15)on the Earcover(7) is used to tune the radio frequency while listening to the radio broadcast program, and no battery room in this side of the headset.

Figure 2:
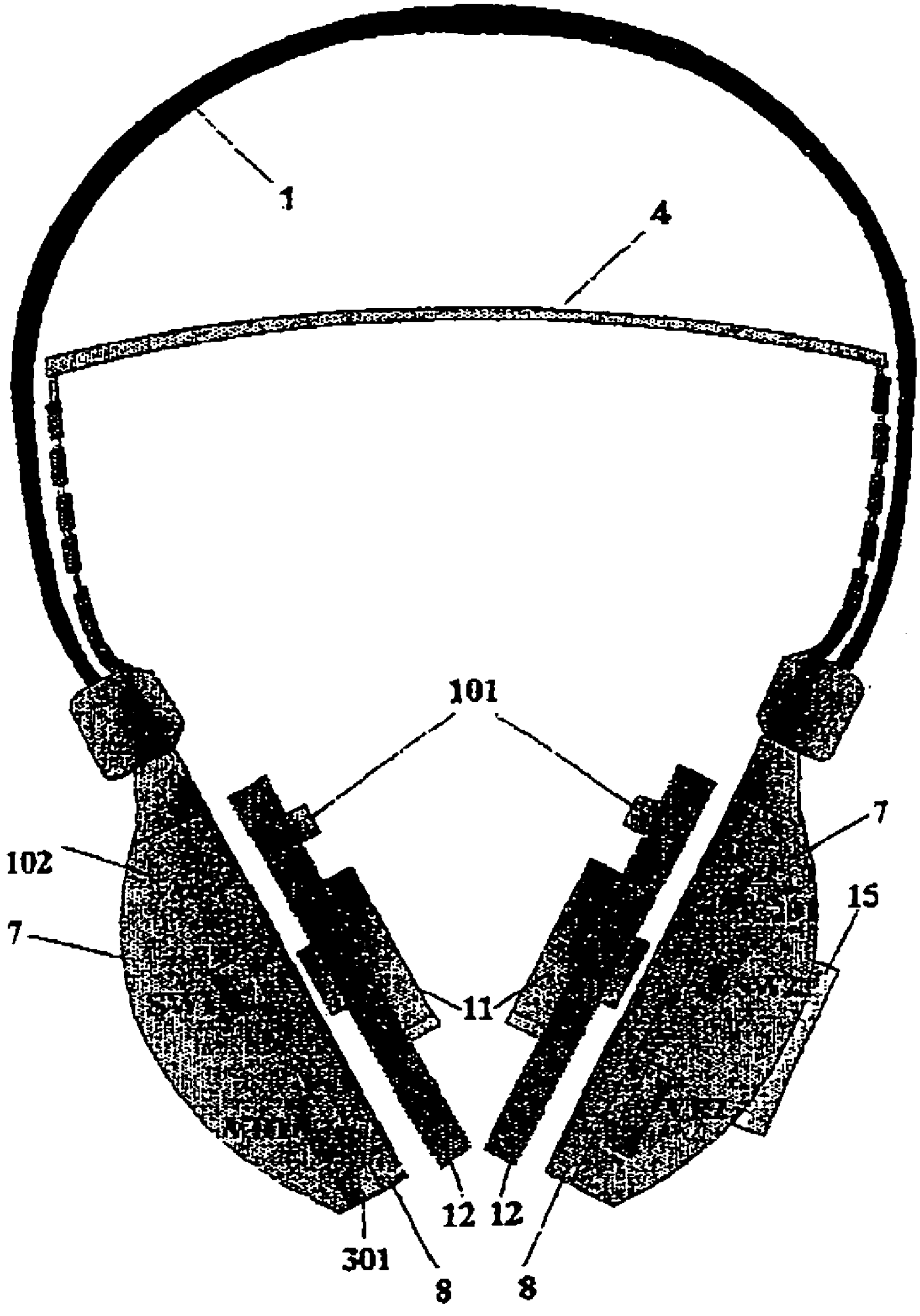
FIG. 2 is a front view of the device of this invention.
Figure 3A:
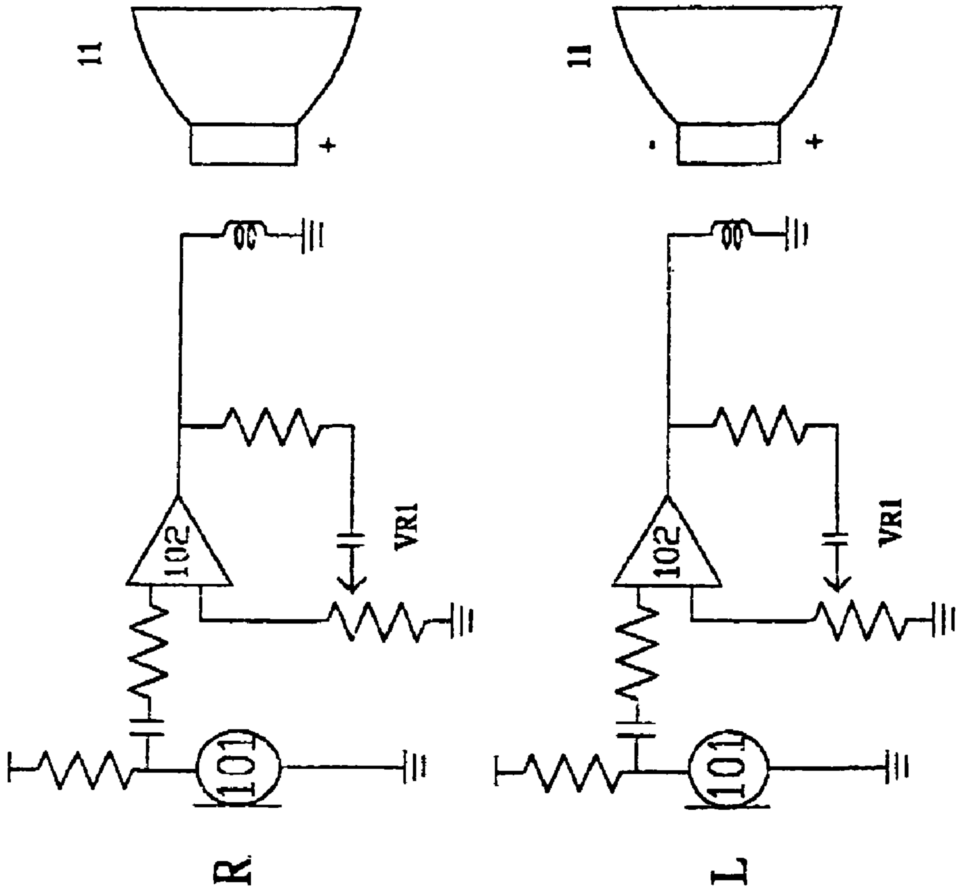
FIG. 3*a* is a circuit diagram for the anti-noise system of this invention.
Figure 3B:
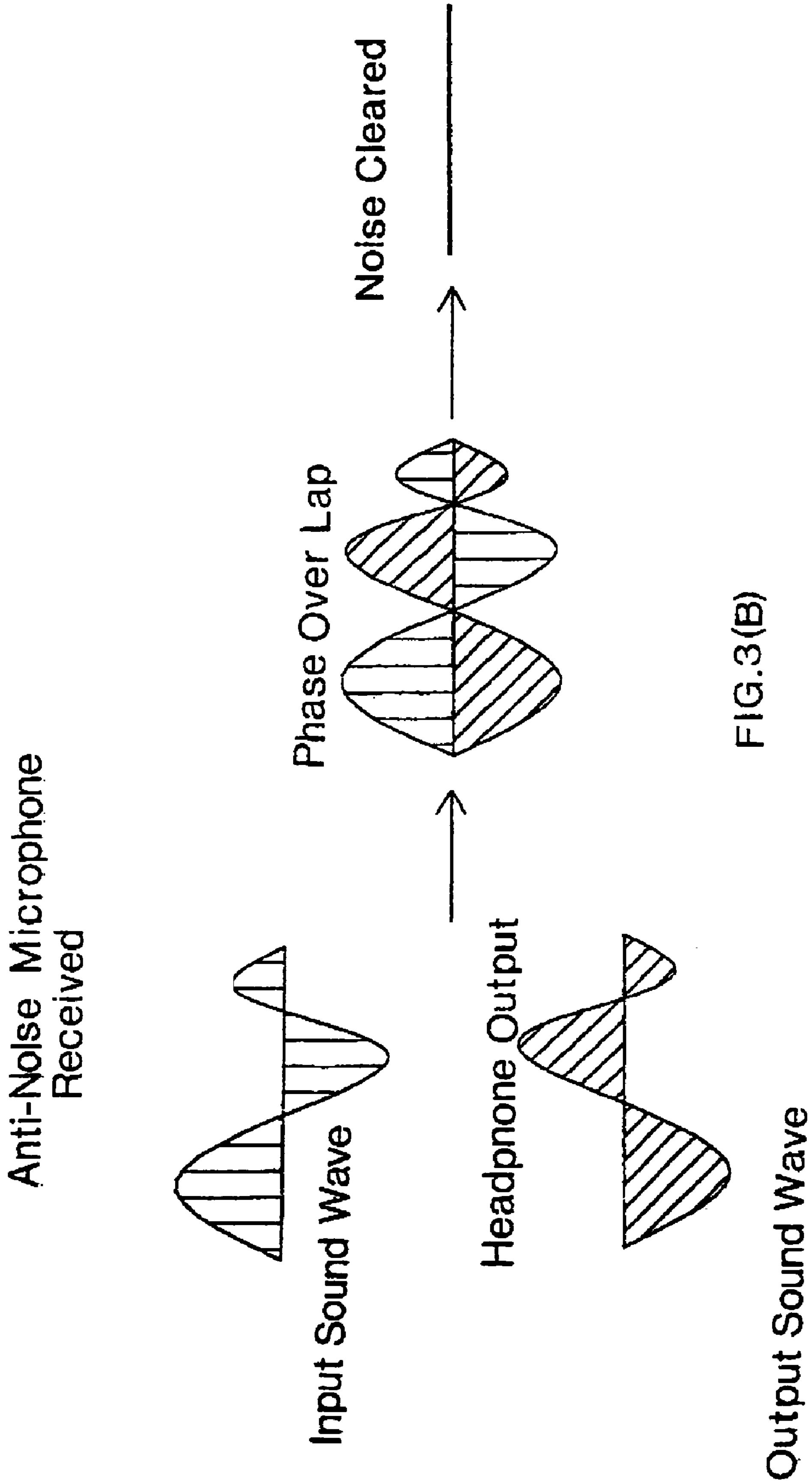
FIG. 3*b* is a schematic representation of the anti-noise system of FIG. 3*a*.
Figure 5:
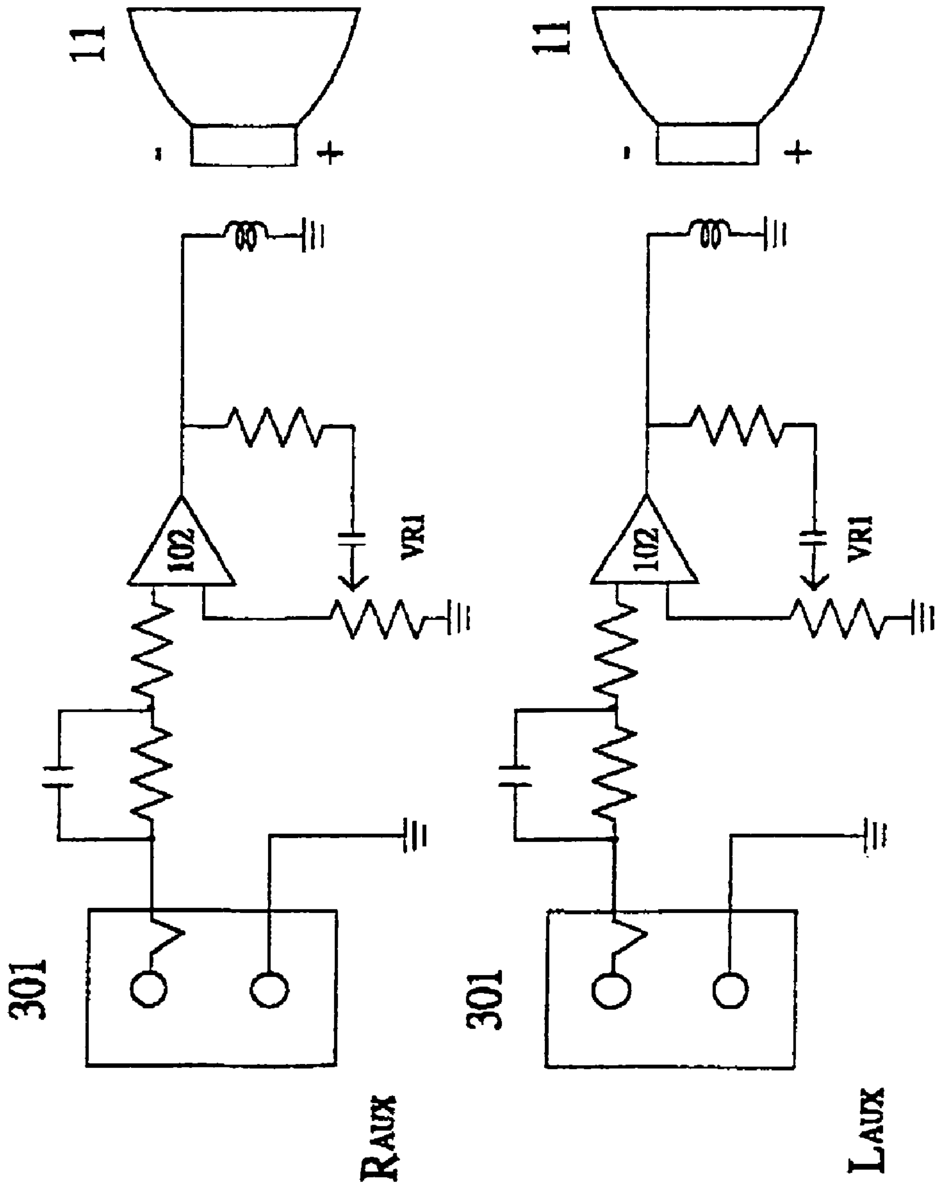
FIG. 5 is a circuit diagram of the sound-collection circuit system of this invention.

FIG. 2 is the out-looking diagram of this invention. On the two sides Speaker Plate (12) of the headphone, there is a speaker (11) to generate sound waves, and a microphone to receive the external noise. The Anti-Noise circuit system of this invention (See FIGS. 3*a* and 3*b*) is on one of the PCB Assembly (8) of the Earcover (7) (The left one as shown in FIG. 2). This PCB consists of a phase detection and u-circuit IC (102), a switch (SWI) and a Variable Resister (VR1) for user to adjust the volume. There is also an External Input Terminal (301) (See FIG. 5) that connected to the PCB to provide the input of the external audio signal.

Figure 4:
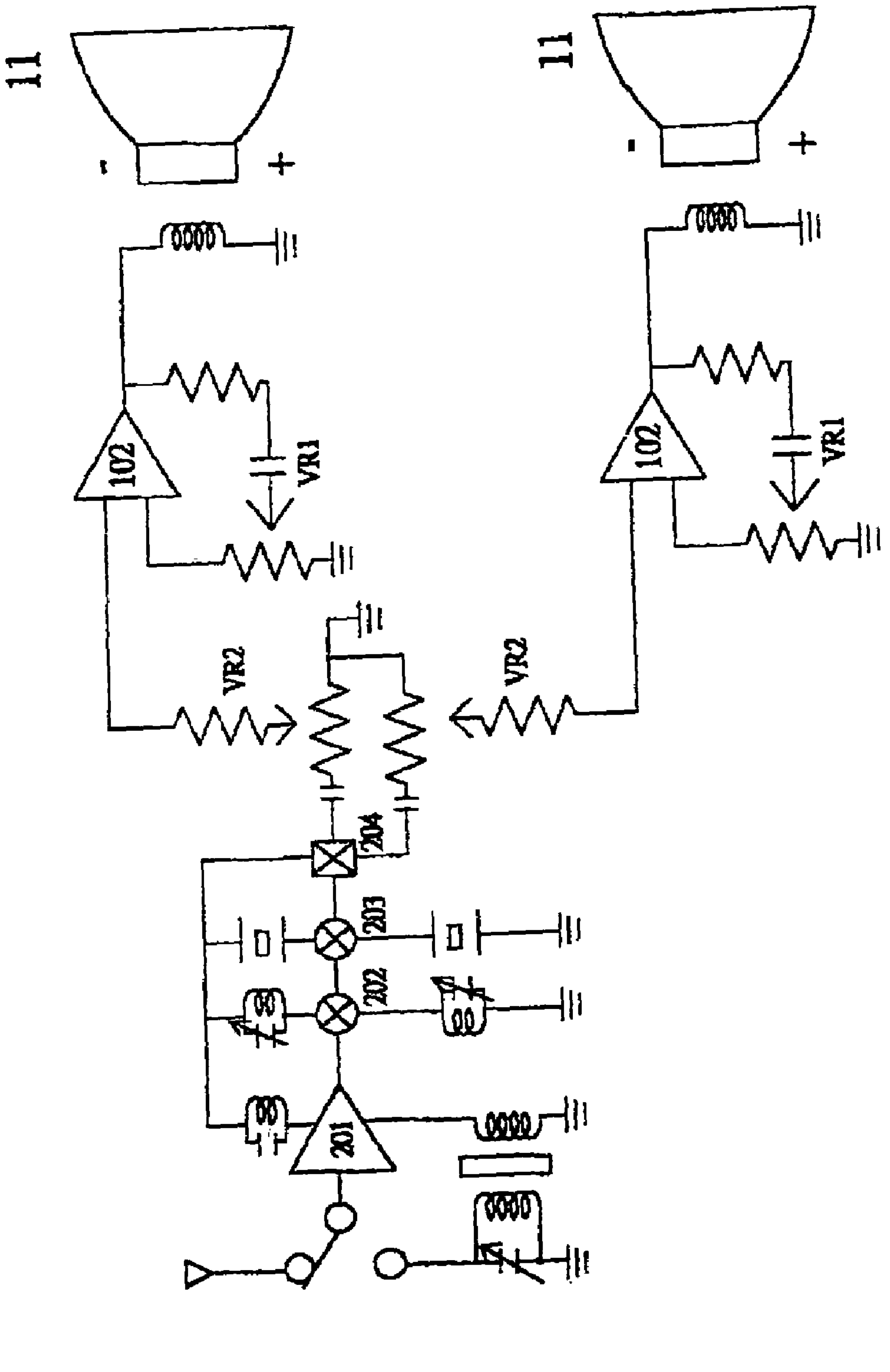
FIG. 4 is a circuit diagram of the radio receiving circuit of this invention.

The FM, AM receiving circuit system (See FIG. 4) is on the other PCB Assembly (8) of the Earcover (7) (The right one as shown in FIG. 2). This PCB consists of a u-circuit IC (201), a switch (SW2), a Variable Resister (VR2) to adjust the volume, and channel tuner to tune the radio frequency . The Cable (3) that connects the two Headsets is hide in the Headband Leading Cable (3). Therefore, it is impossible for the cable to hinder other object except connect to the external audio input source.

Figure 6:
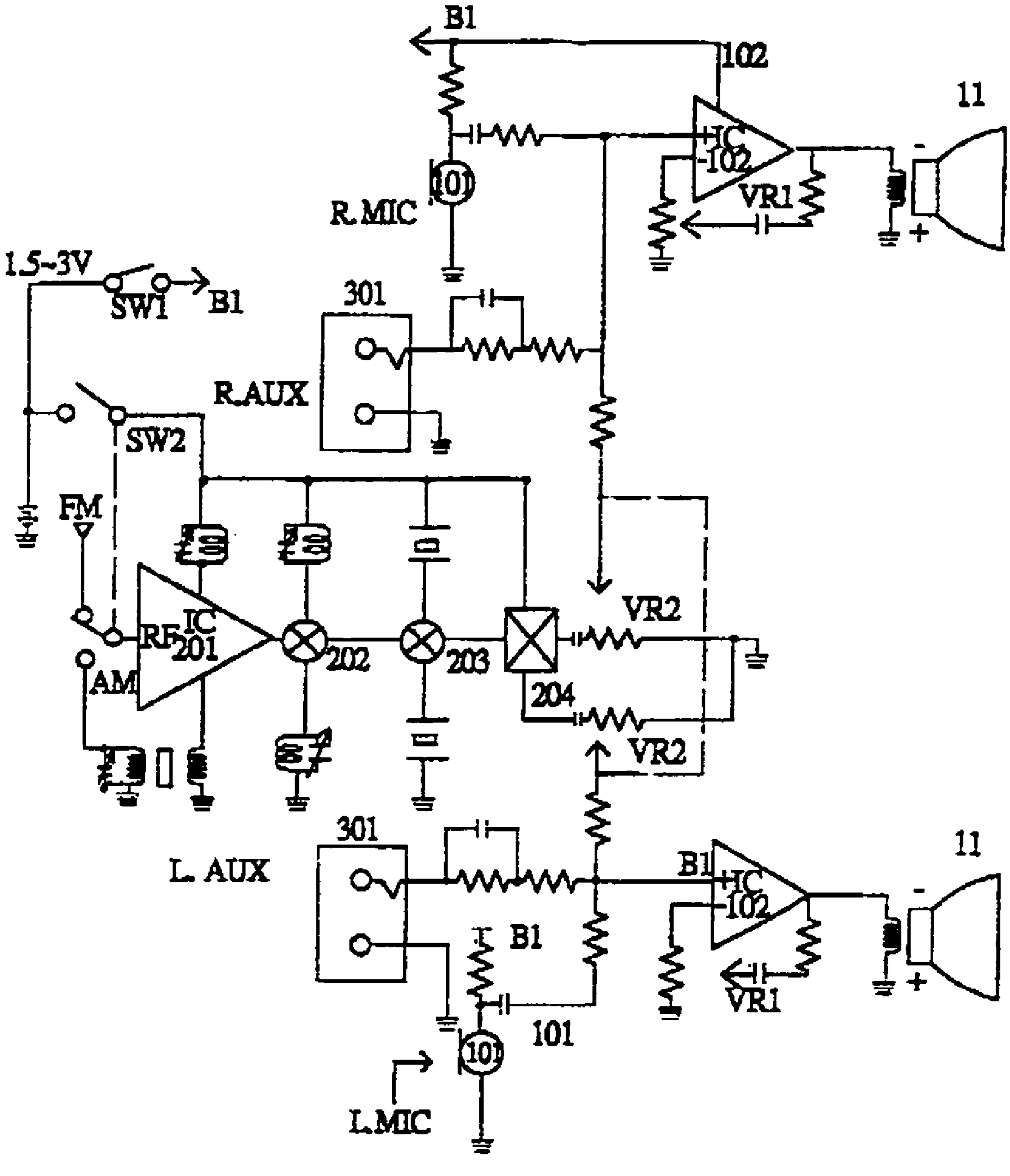
FIG. 6 is a synthesis circuit system of the components of FIGS. 3*a*, 4 and 5.

One of the characteristics of this invention is combining the Anti-Noise circuit system, radio receiving circuit system and sound-collect circuit system into a multi-functional circuit system. The action of each circuit are described as follows:

FIG. 6 is the synthesis circuit that integrated the characteristic of the three circuits described above. The action voltage is from 1.5 V to 3 V and the dynamic sound pressure design is used. The characteri of the synthesis circuit is that the direction of the audio signals are all connected to the Anti-Noise circ system, no matter the signal is from radio receiving circuit or from sound-collect circuit system. Therefore, it not only has the good effective of noise proof but also provides the clearness radio broadcasting program or puerness external audio input, without the interfering of the noise.

In Summary, the present invention "3-in-1 Anti-Noise Radio Sound-Collect device", is a multi-function 3-in-1 design. The wireless feature provides more convenient in usage. Under the noise-polluted environment, it not only protects the user's ears from noise but also provide the user with The radio program and the input of the external audio signal. Furthermore, without taking off the headphone, user can communicate with the other through its microphone sound-collector. Therefore, the novelty, progressive and the high usability of industrial of this new invention makes it qualify in applying a new patent.

What the invention claimed is:

1. A wireless 3-in-1 anti-noise, radio, and sound-collecting device comprising:

a headphone structure having right and left ear cover speakers, a head band interconnecting said speakers, and a PCB installed in said headphone structure; said PCB having first, second and third circuit systems therein;

said first circuit system being an anti-noise circuit comprising a microphone for detecting noise, phase detection U-circuits coupled to said microphone and to each speaker and means for emitting a sound wave of opposite phase to said noise, coupled to said speakers;

said second circuit system being a radio circuit system comprising an am/fm receiver, a U-circuit IC, a down converter circuit, a detect circuit, and a demodulator circuit;

said third circuit system being a sound collection circuit system_comprising an external source audio input terminal, said second circuit system demodulator circuit and said third circuit system audio input terminal being coupled to said phase detecting U-circuits in said first circuit system and to said speakers.

* * * * *